United States Patent
Whitehurst et al.

(10) Patent No.: US 7,596,414 B2
(45) Date of Patent: Sep. 29, 2009

(54) CUFF ELECTRODE ARRANGEMENT FOR NERVE STIMULATION AND METHODS OF TREATING DISORDERS

(75) Inventors: Todd K. Whitehurst, Santa Clarita, CA (US); Kirsten N. Jaax, Saugus, CA (US); Rafael Carbunaru, Studio City, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 617 days.

(21) Appl. No.: 11/294,283

(22) Filed: Dec. 5, 2005

(65) Prior Publication Data

US 2007/0129780 A1 Jun. 7, 2007

(51) Int. Cl.
*A61N 1/05* (2006.01)
(52) U.S. Cl. ..................................................... 607/118
(58) Field of Classification Search .................. 607/118
See application file for complete search history.

(56) References Cited

U.S. PATENT DOCUMENTS

| | | | |
|---|---|---|---|
| 3,941,136 A | 3/1976 | Bucalo | |
| 4,033,357 A | 7/1977 | Helland et al. | |
| 4,135,518 A | 1/1979 | Dutcher | |
| 4,301,815 A | 11/1981 | Doring | |
| 4,542,753 A | 9/1985 | Brenman et al. | |
| 4,585,005 A | 4/1986 | Lue et al. | |
| 4,702,254 A | 10/1987 | Zabara | |
| 4,722,353 A | 2/1988 | Sluetz | |
| 4,796,643 A | 1/1989 | Nakazawa et al. | |
| 4,867,164 A | 9/1989 | Zabara | |
| 4,957,118 A | 9/1990 | Erlebacher | |
| 5,025,807 A | 6/1991 | Zabara | |
| 5,095,905 A * | 3/1992 | Klepinski | 600/377 |
| 5,139,539 A | 8/1992 | Haynes, Jr. | |
| 5,143,067 A * | 9/1992 | Rise et al. | 600/377 |
| 5,193,539 A | 3/1993 | Schulman et al. | |
| 5,193,540 A | 3/1993 | Schulman et al. | |
| 5,239,540 A | 8/1993 | Rovira et al. | |
| 5,282,468 A * | 2/1994 | Klepinski | 600/377 |

(Continued)

FOREIGN PATENT DOCUMENTS

WO    WO 98/37926    9/1998

(Continued)

OTHER PUBLICATIONS

U.S. Appl. No. 11/040,209, filed Jan. 20, 2005 by Colvin et al., for "Implantable Microstimulator with Plastic Housing and Methods of Manufacture and Use" (Not Published).

(Continued)

*Primary Examiner*—Carl H Layno
*Assistant Examiner*—Yun Haeng Lee
(74) *Attorney, Agent, or Firm*—Darby & Darby P.C.; Bruce E. Black

(57) ABSTRACT

One embodiment is a stimulator arrangement for a nerve. The stimulator arrangement includes a cuff for placement around the nerve and a plurality of electrodes disposed on the cuff. The cuff comprises a first edge and defines a plurality of indentations along the first edge of the cuff. The stimulator arrangement may also include a stimulator unit coupled to the electrodes of the cuff. The stimulator unit may also be implantable.

18 Claims, 5 Drawing Sheets

U.S. PATENT DOCUMENTS

| | | | |
|---|---|---|---|
| 5,312,439 | A | 5/1994 | Loeb |
| 5,314,457 | A | 5/1994 | Jeutter et al. |
| 5,376,108 | A | 12/1994 | Collins et al. |
| 5,433,735 | A | 7/1995 | Zanakis et al. |
| 5,439,938 | A | 8/1995 | Snyder et al. |
| 5,454,840 | A | 10/1995 | Krakovsky et al. |
| 5,487,756 | A * | 1/1996 | Kallesoe et al. ............. 607/118 |
| 5,571,118 | A | 11/1996 | Boutos |
| 5,741,319 | A | 4/1998 | Woloszko et al. |
| 5,775,331 | A | 7/1998 | Raymond et al. |
| 5,919,220 | A * | 7/1999 | Stieglitz et al. ............. 607/118 |
| 5,938,584 | A | 8/1999 | Ardito et al. |
| 6,051,017 | A | 4/2000 | Loeb et al. |
| 6,058,332 | A | 5/2000 | Dahl |
| 6,181,969 | B1 | 1/2001 | Gord |
| 6,188,932 | B1 | 2/2001 | Lindegren |
| 6,292,703 | B1 * | 9/2001 | Meier et al. ................. 607/118 |
| 6,516,227 | B1 | 2/2003 | Meadows et al. |
| 6,600,956 | B2 * | 7/2003 | Maschino et al. ........... 607/118 |
| 6,609,029 | B1 | 8/2003 | Mann et al. |
| 6,609,032 | B1 | 8/2003 | Woods et al. |
| 6,650,943 | B1 | 11/2003 | Whitehurst et al. |
| 6,735,474 | B1 | 5/2004 | Loeb et al. |
| 6,741,892 | B1 | 5/2004 | Meadows et al. |
| 6,788,975 | B1 | 9/2004 | Whitehurst et al. |
| 2003/0074039 | A1 * | 4/2003 | Puskas ....................... 607/118 |
| 2004/0010303 | A1 * | 1/2004 | Bolea et al. ................. 607/118 |
| 2004/0059392 | A1 | 3/2004 | Parramon et al. |

FOREIGN PATENT DOCUMENTS

| | | |
|---|---|---|
| WO | WO 98/43700 | 10/1998 |
| WO | WO 98/43701 | 10/1998 |

OTHER PUBLICATIONS

U.S. Appl. No. 11/056,762, filed Feb. 11, 2005 by Tom He, for "An Implantable Microstimulator Having a Separate Battery Unit and Methods of Use Thereof" (Not Published).

U.S. Appl. No. 11/311,502, filed Dec. 19, 2005 by Whitehurst et al., for "Electrode Arrangement for Nerve Stimulation and Methods of Treating Disorders" (Not Published).

U.S. Appl. No. 11/238,240, filed Sep. 29, 2005 by He et al., for "Implantable stimulator with Integrated Plastic Housing/Metal Contacts and Manufacture and Use" (Not Published).

U.S. Appl. No. 11/376,360, filed Mar. 15, 2006 by Carbunaru et al., for "Resorbable Anchor Arrangements for Implantable Devices and Methods of Making and Using" (Not Published).

Rattay, F., "Analysis of Models for External Stimulation of Axons," IEEE Transactions on Biomedical Engineering, BME-33(10):974-977, 1986.

* cited by examiner

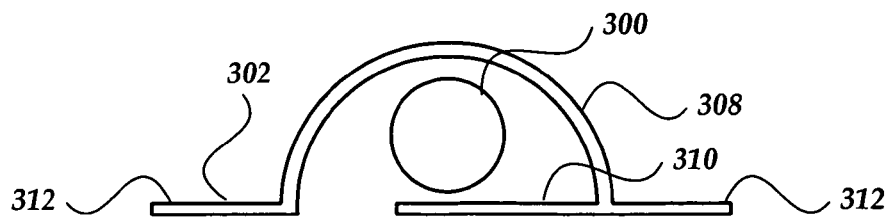
Fig. 1
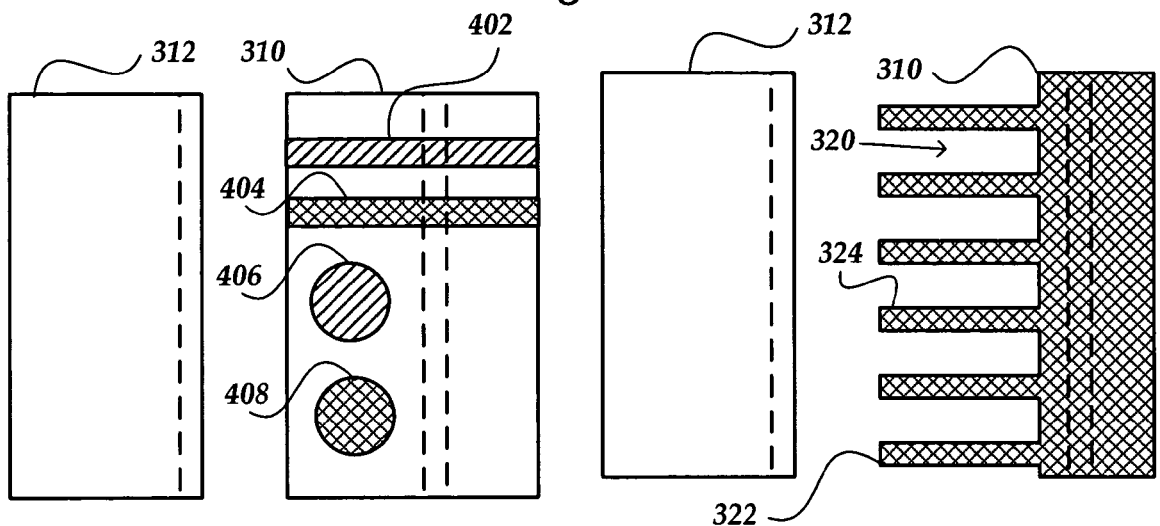
Fig. 2
Fig. 3
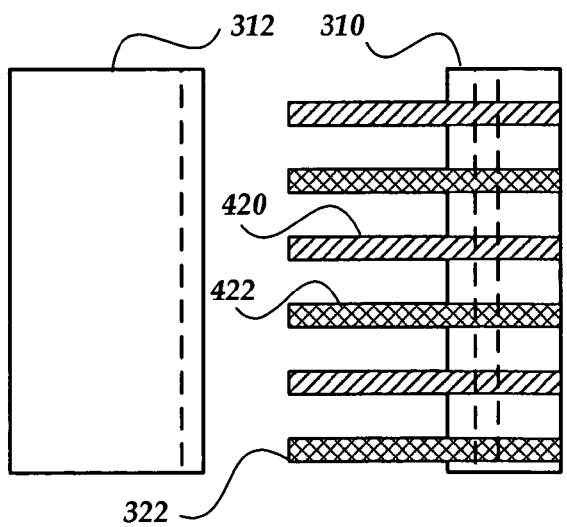
Fig. 4

CUFF ELECTRODE ARRANGEMENT FOR NERVE STIMULATION AND METHODS OF TREATING DISORDERS

FIELD

The invention is directed to electrode arrays, as well as devices containing the electrode arrays, for nerve stimulation and treatment of disorders and methods of manufacture and use. In addition, the invention is directed to electrode arrays in a cuff arrangement, as well as devices containing the electrode arrays and methods of manufacture and use.

BACKGROUND

Epilepsy is characterized by a tendency to recurrent seizures that can lead to loss of awareness or consciousness, disturbances of movement, sensation (including vision, hearing, and taste), autonomic function, mood, and mental function. Epilepsy afflicts 1-2% of the population of the developed world. The mean prevalence of active epilepsy (i.e., continuing seizures or the need for treatment) in developed and undeveloped countries combined is estimated to be 7 per 1,000 of the general population, or approximately 40 million people worldwide. Studies in developed countries suggest an annual incidence of epilepsy of approximately 50 per 100,000 of the general population. However, studies in developing countries suggest this figure is nearly double at 100 per 100,000.

Vagus nerve stimulation (VNS) has been applied with partial success in patients with refractory epilepsy. In this procedure, an implantable pulse generator is implanted in the patient's thorax, and an electrode lead is routed from the generator to the left vagus nerve in the neck. Helix-shaped stimulation and indifferent electrodes are attached to the vagus nerve via an invasive surgical process that requires the carotid sheath to be fully exposed. Based on a number of studies, approximately 5% of patients undergoing VNS are seizure-free, and an additional 30-40% of patients have a greater than 50% reduction in seizure frequency. However, VNS may lead to significant side effects. The vagus nerve provides parasympathetic innervation to the cardiac tissue, and thus VNS may lead to bradycardia, arrhythmia, or even graver cardiac side effects. In fact, VNS systems are often only used on the left vagus nerve, as the right vagus nerve contributes significantly more to cardiac innervation. Additionally, VNS may interfere with proper opening of the vocal cords, which has led to hoarseness and shortness of breath in a significant number of VNS patients.

As another example of a nerve disorder, recent estimates suggest that the number of U.S. men with erectile dysfunction may be near 10-20 million, and inclusion of individuals with partial erectile dysfunction increases the estimate to about 30 million. Electrical stimulation can be used to treat erectile dysfunction. The targets of electrical stimulation are the cavernous nerves. The cavernous nerves run bilaterally between the prostate and the rectum as they course from the sacral spinal cord to the corpora cavernosa in the penis. Near the rectum the nerves form more of a plexus than a coherent nerve, and they are interlaced with small arteries and veins as well as fatty tissue. This collection of small nerve fibers, arteries, and veins can be referred to as the neurovascular bundle.

BRIEF SUMMARY

One embodiment is a stimulator arrangement for a nerve. The stimulator arrangement includes a cuff for placement around the nerve and a plurality of electrodes disposed on the cuff. The cuff comprises a first edge and defines a plurality of indentations along the first edge of the cuff. The stimulator arrangement may also include a stimulator unit coupled to the electrodes of the cuff. The stimulator unit may also be implantable.

Another embodiment is another stimulator arrangement for a nerve. The stimulator arrangement includes a cuff comprising a first curved portion configured and arranged to be disposed over a first portion of the nerve and a second flat portion configured and arranged to be disposed over a second portion of the nerve opposite the first portion. A plurality of electrodes are disposed on the cuff. The stimulator arrangement may also include a stimulator unit coupled to the electrodes of the cuff. The stimulator unit may also be implantable.

Yet another embodiment is a method of stimulating a nerve by disposing a cuff around the nerve. The cuff includes a first edge and defines a plurality of indentations along the first edge of the cuff. A plurality of electrodes are disposed on the cuff. The cuff is coupled to a stimulator unit and electrical signals are provided from the stimulator unit to the electrodes of the cuff to stimulate the nerve.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 1 is a schematic cross-sectional view of one embodiment of a cuff for use in a stimulator device, according to the invention;

FIG. 2 is a schematic top view of one embodiment of a portion of the cuff of FIG. 1, according to the invention;

FIG. 3 is a schematic top view of another embodiment of a portion of the cuff of FIG. 1, according to the invention;

FIG. 4 is a schematic top view of a third embodiment of a portion of the cuff of FIG. 1, according to the invention;

DETAILED DESCRIPTION

Figure 5:
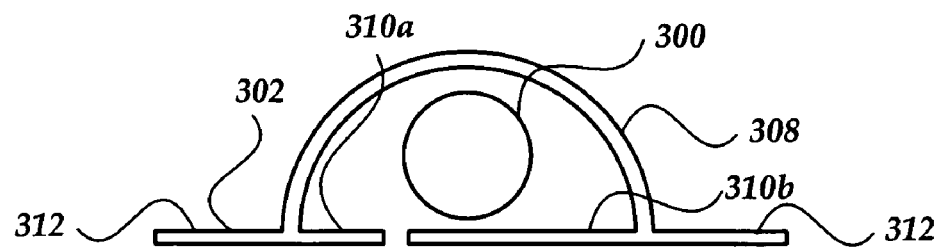
FIG. 5 is a schematic cross-sectional view of another embodiment of a cuff for use in a stimulator device, according to the invention.

The invention is directed to electrode arrays, as well as devices containing the electrode arrays, for nerve stimulation and treatment of disorders. In addition, the invention is directed to implantable stimulator devices with remote electrode arrays in a cuff arrangement and treatment of disorders. For example, the implantable stimulator devices can be used to stimulate the vagus nerve to treat epilepsy or other disorders or to stimulate the cavernous nerve to treat erectile dysfunction or other disorders. Stimulation of the vagus or cavernous nerve are described herein as examples of use of the inventive implantable stimulator devices; however, it will be recognized that the implantable stimulator devices and stimulator components disclosed herein can be used to stimulate other nerves and tissues.

Electrode arrays can be disposed near or adjacent a nerve to stimulate the nerve, such as, for example, the left vagus nerve or the cavernous nerve. In some instances, however, it is more convenient and/or advantageous to implant a stimulator unit, such as a microstimulator, elsewhere and then couple the stimulator unit, via a lead, to electrodes disposed around or near the nerve. For example, implanting the stimulator unit elsewhere may be desirable so that the stimulator unit is not disposed in the highly mobile neck or groin region where the stimulator unit might be dislodged or otherwise moved from the original implanted position. In addition or alternatively, the stimulator unit may be implanted elsewhere to provide an easier site for removal of the stimulator unit if it should malfunction, cease functioning, or otherwise require replacement or removal. Finally, the stimulator unit may be implanted at a site where a rechargeable battery, if present, can be easily and/or inconspicuously recharged.

Examples of suitable implantable stimulator devices, including microstimulators, that can be used or modified for use in stimulating the nerve include, but are not limited to, stimulator devices described in U.S. Pat. Nos. 5,139,539; 5,239,540; 5,312,439; 6,051,017; and 6,609,032; U.S. Patent Application Publication No. 2004/059392; U.S. patent application Ser. Nos. 11/040,209 and Ser. No. 11/056,762; and PCT Patent Applications Publication Nos. 98/37926; 98/43700; and 98/43701, all of which are incorporated herein by reference.

FIGS. 1-8 show embodiments of a cuff 302 for use with a separate stimulator unit. The cuff 302 includes two or more electrodes that are coupled, via a lead 350 (FIG. 10) to a stimulator unit and provide electrical stimulation to the selected nerve. The cuff 302 is disposed around the nerve 300. The cuff can be formed to curve around most or all of the nerve or the cuff can be formed with a curved first portion 308 that is disposed around a first portion of the nerve 300 and a relatively flat second portion 310 that is disposed around a second portion of the nerve. For example, the second portion 310 of the cuff 302 can be positioned between the cavernous nerve and the rectum to facilitate stimulation of the cavernous nerve to treat erectile dysfunction or other disorders. Placing the cuff around all or most of the nerve (or neurovascular bundle) can facilitate recruitment of more of the nerve tissue for stimulation.

The electrodes can be positioned on either the first or second portions of the cuff or any combination of the first and second portions. The cuff typically includes one or more anodes and one or more cathodes. The number of anodes and cathodes may be the same or different. The definition of which electrodes are anodes and which are cathodes may be constant or can be altered by the stimulator unit during operation of the stimulator device. The anodes and cathodes can be positioned in any relationship with respect to each other. The relationship may depend on the application. When multiple anodes (or cathodes) are used, the anodes (or cathodes), or a subset thereof, can be electrically connected to each other at the cuff or the lead or they may be each independently connected to the stimulator unit. Independent control of each electrode can be particularly useful for steering the current produced by the cuff to provide selective stimulation of desired portions (e.g., bundles of axons) of the nerve.

FIG. 5 illustrates one embodiment in which the second portion 310 is divided into two parts 310a, 310b. These parts may be equal or unequal in length. The cuff 302 may include one or more additional third portions 312 that extend away from the nerve and can facilitate stability of the cuff, connection to the lead, or attachment of the cuff 302 to surrounding tissue.

FIGS. 2-4 and 6-8 schematically illustrate embodiments of the second and third portions 310, 312 of the cuff (with possible attachment sites of the first portion 308 indicated by dotted lines.) FIG. 2 illustrates one embodiment, as well as illustrating possible electrode configurations including strip electrodes 402, 404 and button electrodes 406, 408. The button electrodes can be provided in shapes other than circular. Any combination of strip electrodes and button electrodes can be used including combinations with only strip electrodes or only button electrodes.

FIG. 3 illustrates one embodiment with indentations 320 formed along a first edge 322 of the second portion 310. The length and width of these indentations 320, and corresponding extensions 324, can be selected based on a variety of factors including, for example, stability, manufacturability, the nerve to be stimulated, the size of the nerve, the size of the cuff, the desired current density, the implantation site, and the like. FIG. 3 also illustrates another possible electrode arrangement in which the second portion 310 (or a part of the second portion) forms a single electrode. The opposite electrode can be formed, for example, by the first portion 308 of the cuff or a second part of the second portion 310 (see, for example, FIG. 6.)

FIG. 4 illustrates yet another embodiment in which different extensions are assigned to be different electrodes 420, 422. In one embodiment, the extensions form alternating anode(s) and cathode(s), as illustrated in FIG. 4.

Figure 6:
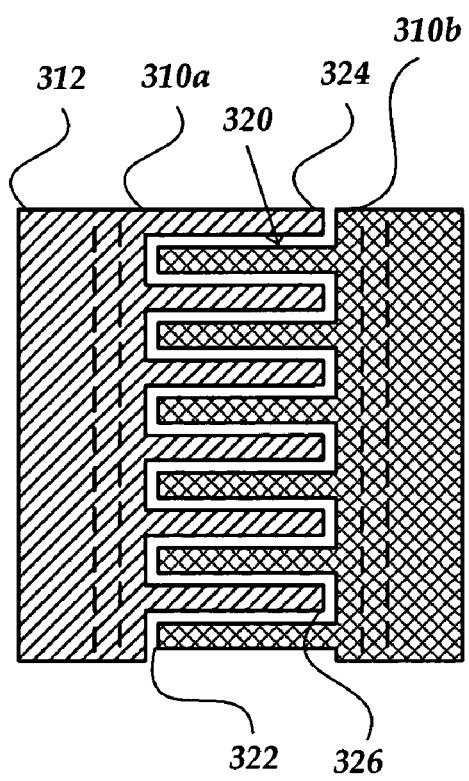
FIG. 6 is a schematic top view of one embodiment of a portion of the cuff of FIG. 5, according to the invention.
Figure 7:
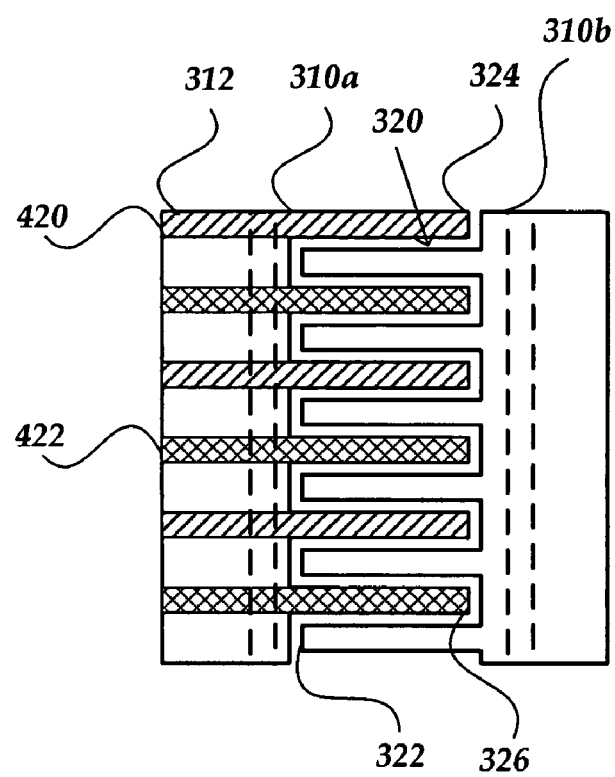
FIG. 7 is a schematic top view of another embodiment of a portion of the cuff of FIG. 5, according to the invention.
Figure 8:
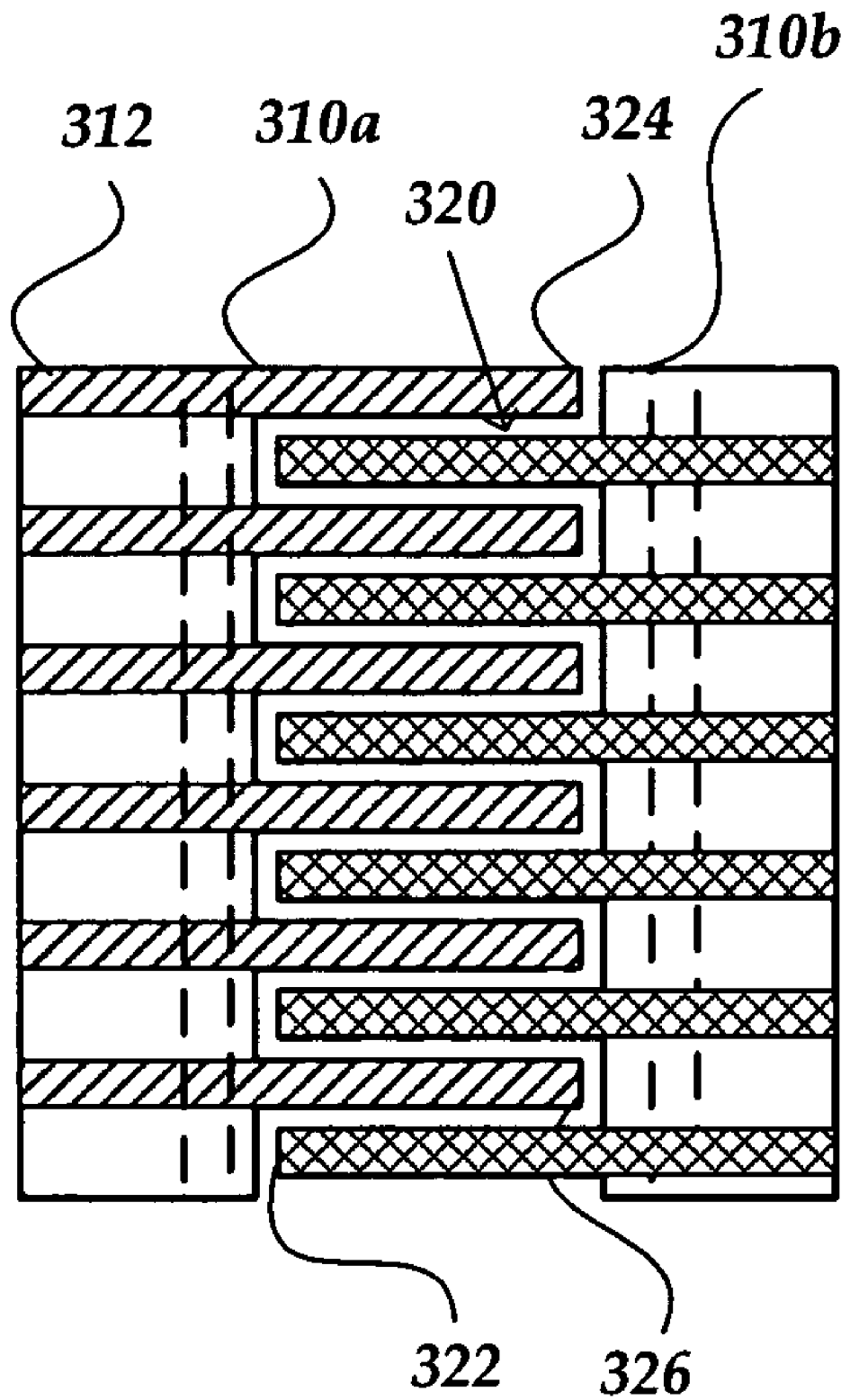
FIG. 8 is a schematic top view of a third embodiment of a portion of the cuff of FIG. 5, according to the invention.

FIG. 6 illustrates another embodiment with the second portion 310 of the cuff 302 including two parts 310a, 310b with each part having indentations 320, and corresponding extensions 324, formed along edges 322, 326. In this embodiment, the indentations 320 of parts 310a, 310b interdigitate, although non-interdigitating indentations could also be used. Also, as illustrated in FIG. 6, the two parts 310 and 310b can be separate electrodes (e.g., one part is a cathode and the other part is an anode.) FIG. 7 illustrates yet another interdigitating embodiment in which different indentations of the same part 310a form different electrodes (e.g., one or more cathodes 420 and one or more anodes 422.) FIG. 8 illustrates another interdigitating embodiment in which individual electrodes are interdigitated. In a variation on this arrangement, only some of the interdigitated extensions contain electrodes. This can be used to produce monopolar, bipolar, tripolar, etc. arrangements of electrodes.

The electrodes are formed of a conductive material. Preferably, the electrodes are formed of a material that does not substantially corrode under the operating conditions and in the operating environment for the expected lifetime of the stimulator device. Examples of suitable materials include metals, alloys, conductive plastics, and other conductive materials such as, for example, titanium, iridium, platinum, platinum iridium, stainless steel, and the like.

The electrodes can be formed entirely of a single conductive material, such as a metal or alloy, or one or both of the electrodes can be formed using a combination of conductive materials such as, for example, a conductive coating over a bulk metallic electrode. In other embodiments, one or both of the electrodes can be formed from a polymeric material that is at least partially, or fully, coated with a conductive coating, such as a metal, alloy, or conductive oxide (e.g., iridium tin oxide) coating.

The cuff can be formed using a plastic or cloth material with conductors disposed in or on the material and coupled between the electrodes and the lead. The cuff should be biocompatible and not substantially degrade during the expected implantation period. The cuff can be formed using any method including, for example, molding. The electrodes can be coupled to the cuff by any method including molding the cuff around the electrodes and electrode conductors that go to the lead or by attaching the electrodes to the cuff by adhesive or other attachment methods.

Figure 10:
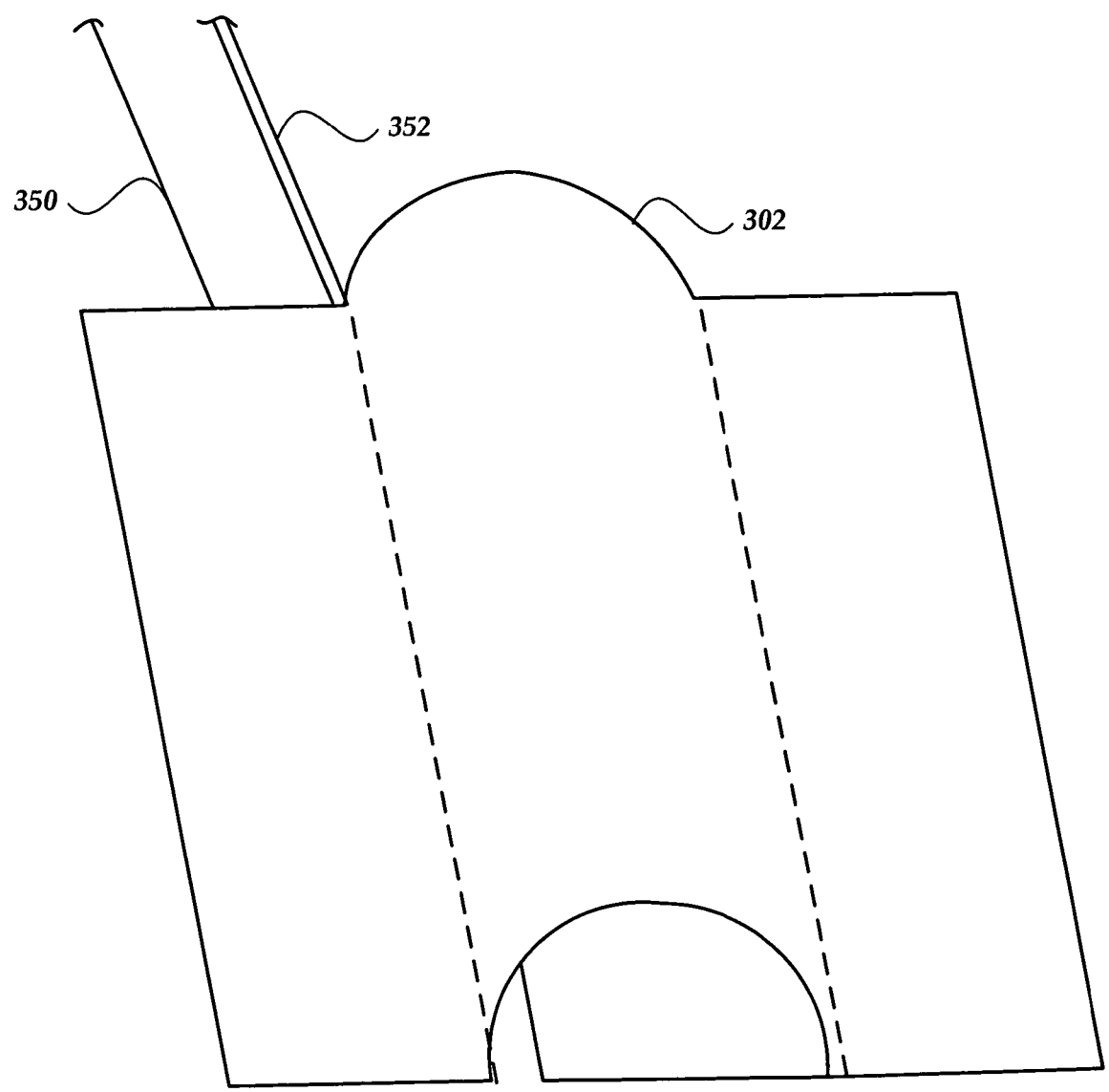
FIG. 10 is a perspective view of one embodiment of a cuff for use in a stimulator device, according to the invention.

In addition, the cuff 302 or lead optionally includes one or more lumens 352 entering the cuff and with corresponding opening(s) through which a drug can be infused to the nerve or adjacent tissue, as illustrated in FIG. 10. The lumens can connect through the lead to the microstimulator unit or a separate drug infusion unit that contains a reservoir of the drug and a pump that can provide the drug on a continuous, regular, irregular, or "as needed" basis. A processor may be provided to control the pump. The processor is optionally programmable from an external source by transmitting signals to the drug infusion processor. As an alternative, the lumen(s) can be accessed externally to infuse the drug using a drug infusion unit that is positioned on the skin of the patient or elsewhere or the lumen can be accessed to provide periodic infusions using a needle or the like.

Optionally, the cuff can also include one or more electrodes or sensors that are used to detect or measure the state of the nerve, the state of the erectile dysfunction or other disorder, or the state of the patient. These electrodes or sensors can be observed by the microstimulator unit or a separate control unit.

Figure 9:
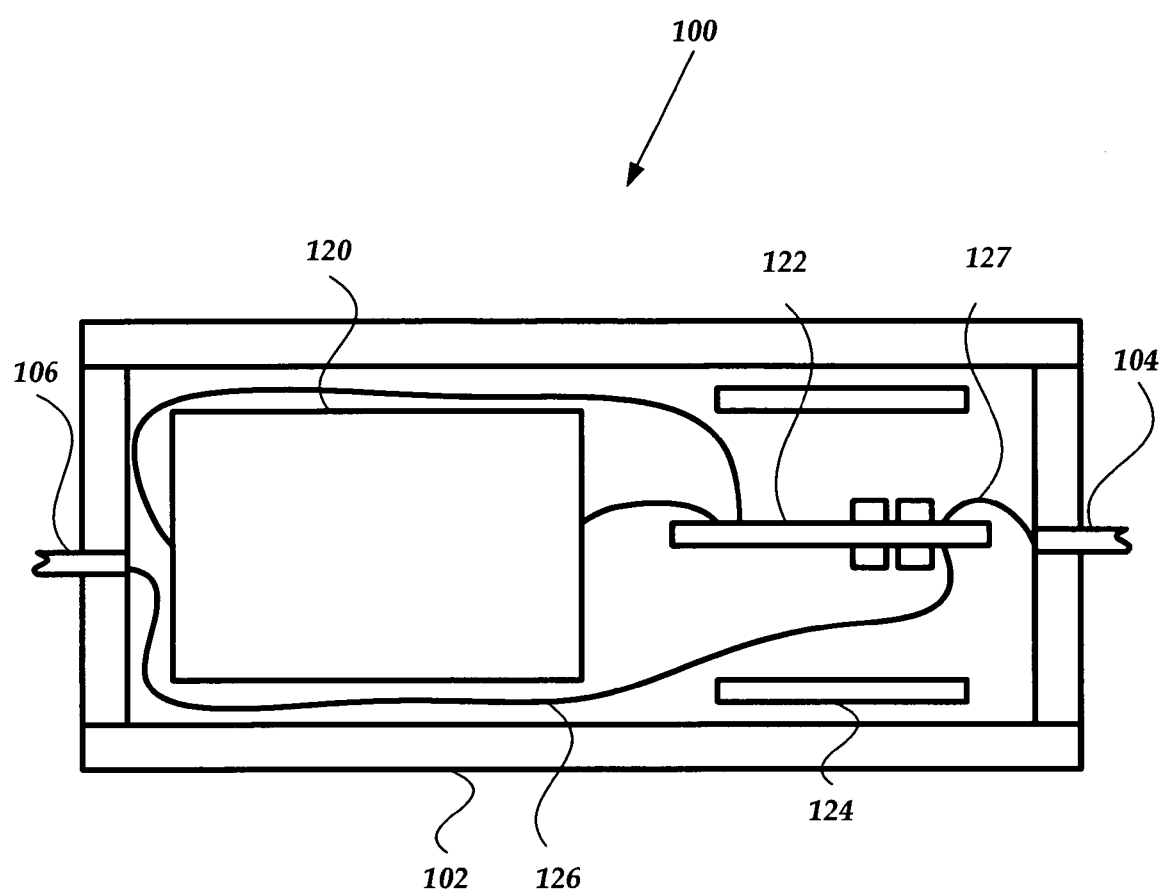
FIG. 9 is a schematic cross-sectional view of one embodiment of a stimulator unit, according to the invention.

An implantable microstimulator includes an implantable microstimulator unit, a cuff that is disposed around or near the nerve and contains electrodes, and a lead coupling the implantable microstimulator unit to the electrodes on the cuff. FIG. 9 illustrates one embodiment of an implantable stimulator unit 100. The implantable stimulator unit 100 includes a housing 102, electrode conductors 104, 106 to couple to the electrode arrangement, a power source 120, an electronics subassembly 122, and an optional antenna 124. Other embodiments of an implantable stimulator unit may include more or fewer components. It will be understood that the power source 120 and/or components of the electronics subassembly 122 and/or the optional antenna 124 can be provided outside of the housing in a separate unit and coupled to the implantable stimulator unit by a lead. The electronic subassembly 122 provides the electronics used to operate the stimulator device and generate the electrical pulses at the electrode arrangement to produce stimulation of the nerve.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A stimulator arrangement for a nerve, comprising:
   a cuff configured and arranged to be placed around the nerve, the cuff comprising a curved portion, a flat portion, the flat portion extending away from the nerve, a first part having a first edge and defining a plurality of indentations along the first edge of the cuff; and
   a plurality of electrodes disposed on the cuff.

2. The stimulator arrangement of claim 1, wherein a first electrode of the plurality of electrodes is disposed along the first edge.

3. The stimulator arrangement of claim 1, wherein the cuff further comprises a second part having a second edge opposing the first edge of the first part, the second edge defining a plurality of indentations along the second edge.

4. The stimulator arrangement of claim 3, wherein the indentations of the first and second edges interdigitate.

5. The stimulator arrangement of claim 4, wherein the plurality of electrodes comprises alternating anodes and cathodes defined by the interdigitated indentations of the first and second edges.

6. The stimulator arrangement of claim 3, wherein a first electrode of the plurality of electrodes is disposed along the first edge and a second electrode of the plurality of electrodes is disposed along the second edge.

7. The stimulator arrangement of claim 3, wherein a first plurality of the plurality of electrodes is disposed along the first edge.

8. The stimulator arrangement of claim 3, wherein a second plurality of the plurality of electrodes is disposed along the second edge.

9. The stimulator arrangement of claim 1, further comprising a stimulator unit coupled to the plurality of electrodes.

10. A stimulator arrangement for a nerve, comprising:
    a cuff comprising a first curved portion configured and arranged to be disposed over a first portion of the nerve, a second flat portion configured and arranged to be disposed over a second portion of the nerve opposite the first portion, and a third flat portion extending away from the nerve; and
    a plurality of electrodes disposed on the cuff.

11. The stimulator arrangement of claim 10, further comprising a stimulator unit coupled to the plurality of electrodes to provide electrical signals to the plurality of electrodes.

12. The stimulator arrangement of claim 10, wherein the second flat portion comprises a first edge having indentations formed along the first edge.

13. The stimulator arrangement of claim 10, wherein the second flat portion comprises a first part comprising the first edge and a second part comprising a second edge that opposes the first edge and has indentations formed along the second edge.

14. The stimulator arrangement of claim 13, wherein the indentation of the first edge are interdigitated with the indentations of the second edge.

15. A method of stimulating a nerve, the method comprising:
    providing the stimulator arrangement of claim 1;
    disposing the cuff of the stimulator arrangement around the nerve coupling the cuff to a stimulator unit; and
    providing electrical signals from the stimulator unit to the electrodes of the cuff to stimulate the nerve.

16. The method of claim 15, wherein the nerve is a vagus nerve and disposing the cuff around the nerve comprises disposing the cuff around the vagus nerve.

17. The method of claim 15, wherein the nerve comprises a cavernous nerve and disposing the cuff around the nerve comprises disposing the cuff around a neurovascular bundle comprising the vagus nerve.

18. The method of claim 15, further comprising implanting the stimulator unit in a portion of the body separated from the nerve.

* * * * *

UNITED STATES PATENT AND TRADEMARK OFFICE
CERTIFICATE OF CORRECTION

PATENT NO. : 7,596,414 B2 Page 1 of 1
APPLICATION NO. : 11/294283
DATED : September 29, 2009
INVENTOR(S) : Whitehurst et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 893 days.

Signed and Sealed this

Twenty-eighth Day of September, 2010

David J. Kappos
*Director of the United States Patent and Trademark Office*